United States Patent
Ben-Ari et al.

(10) Patent No.: US 9,918,686 B2
(45) Date of Patent: Mar. 20, 2018

(54) AUTOMATED FIBRO-GLANDULAR (FG) TISSUE SEGMENTATION IN DIGITAL MAMMOGRAPHY USING FUZZY LOGIC

(71) Applicant: International Business Machines Corporation, Armonk, NY (US)

(72) Inventors: Rami Ben-Ari, Kiryat-Ono (IL); Aviad Zlotnick, Mitzpeh Netofa (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/941,954

(22) Filed: Nov. 16, 2015

(65) Prior Publication Data

US 2017/0135660 A1    May 18, 2017

(51) Int. Cl.
    *G06K 9/00*    (2006.01)
    *A61B 6/00*    (2006.01)
    *G06T 7/00*    (2017.01)

(52) U.S. Cl.
    CPC ............ *A61B 6/502* (2013.01); *G06T 7/0012* (2013.01); *G06T 7/0081* (2013.01); *G06T 2207/30068* (2013.01); *G06T 2207/30096* (2013.01)

(58) Field of Classification Search
    CPC ..... A61B 6/502; G06T 7/0012; G06T 7/0081; G06T 2207/30068; G06T 2207/30096
    See application file for complete search history.

(56) References Cited

U.S. PATENT DOCUMENTS

| | | | | |
|---|---|---|---|---|
| 6,138,045 | A * | 10/2000 | Kupinski | G06T 7/0012 378/37 |
| 7,466,848 | B2 * | 12/2008 | Metaxas | A61B 5/055 382/128 |
| 7,903,861 | B2 | 3/2011 | Luo et al. | |
| 8,315,446 | B2 | 11/2012 | Raundahl et al. | |
| 8,582,858 | B2 * | 11/2013 | Su | G06T 7/238 382/128 |
| 8,675,933 | B2 | 3/2014 | Wehnes et al. | |
| 2006/0177125 | A1 | 8/2006 | Chan et al. | |
| 2013/0272595 | A1 | 10/2013 | Heine et al. | |
| 2013/0281840 | A1 | 10/2013 | Vaughan et al. | |
| 2014/0082542 | A1 | 3/2014 | Zhang et al. | |
| 2015/0071521 | A1 | 3/2015 | Wehnes et al. | |

FOREIGN PATENT DOCUMENTS

| | | |
|---|---|---|
| EP | 2807630 B1 | 6/2015 |
| WO | 2015077076 A1 | 5/2015 |

OTHER PUBLICATIONS

Saha et al., "Breast Tissue Density Quantification Via Digitized Mammograms," IEEE, Aug. 2001, pp. 792-803.*

(Continued)

*Primary Examiner* — Shefali Goradia
(74) *Attorney, Agent, or Firm* — Gilbert Harmon, Jr.

(57) ABSTRACT

Embodiments of the present invention provide automated systems and methods for segmentation of fibro-glandular (FG) tissue in digital mammography. A classifier is trained for breast density without the prior knowledge for FG tissue. The classifier is then used for feature selection, where the selected features are fed into a fuzzy logic module, and an adaptive threshold is obtained. Post-processing is performed on the image in order to reduce regions which may have been misclassified during the FG segmentation.

17 Claims, 8 Drawing Sheets

(56) References Cited

OTHER PUBLICATIONS

Breiman, "Random Forests", Machine Learning, 45, 5-32, 2001, 28 pages, © 2001 Kluwer Academic Publishers, The Netherlands.

Javed et al., "Fuzzy Logic and Local Features Based Medical Image Segmentation", ICIP 2013, pp. 1148-1152, © 2013 IEEE.

Kallenberg et al., "Automatic breast density segmentation: an integration of different approaches", Physics in Medicine and Biology 56 (2011), Published Apr. 5, 2011, pp. 2715-2729, © 2011 Institute of Physics and Engineering in Medicine, UK.

Keller et al., "Adaptive Multi-cluster Fuzzy C-Means Segmentation of Breast Parenchymal Tissue in Digital Mammography", MICCAI 2011, Part III, LNCS 6893, 2011, pp. 562-569, © Springer-Verlag Berlin Heidelberg 2011.

Keller et al., "Estimation of breast percent density in raw and processed full field digital mammography images via adaptive fuzzy c-means clustering and support vector machine segmentation", Medical Physics, vol. 39, No. 8, Aug. 2012, pp. 4903-4917, © 2012 Am. Assoc. Phys. Med.

Mustra et al., "Breast Density Classification Using Multiple Feature Selection", AUTOMATIKA 53(4), 2012, pp. 362-372.

Oliver et al., "A Novel Breast Tissue Density Classification Methodology", IEEE Transactions on Information Technology in Biomedicine, vol. 12, No. 1, Jan. 2008, pp. 55-65.

Petroudi et al., "Automatic Classification of Mammographic Parenchymal Patterns: A Statistical Approach", Proceedings of the 25th Annual International Conference of the IEEE Engineering in Medicine and Biology Society, vol. 1, 2003, pp. 798-801.

Petroudi et al., "Breast Density Segmentation Using Texture", IWDM 2006, LNCS 4046, 2006, pp. 609-615, © Springer-Verlag Berlin Heidelberg 2006.

Torrent et al., "Breast Density Segmentation: A Comparison of Clustering and Region Based Techniques", IWDM 2008, LNCS 5116, 2008, pp. 9-16, © Springer-Verlag Berlin Heidelberg 2008.

Wu et al., "Automated fibroglandular tissue segmentation and volumetric density estimation in breast MRI using an atlas-aided fuzzy C-means method", Medical Physics, vol. 40, No. 12, Dec. 2013, pp. 122302-1-122302-12, © 2013 Am. Assoc. Phys. Med.

Zadeh, "Fuzzy Sets", Information and Control 8, 1965, pp. 338-353.

* cited by examiner

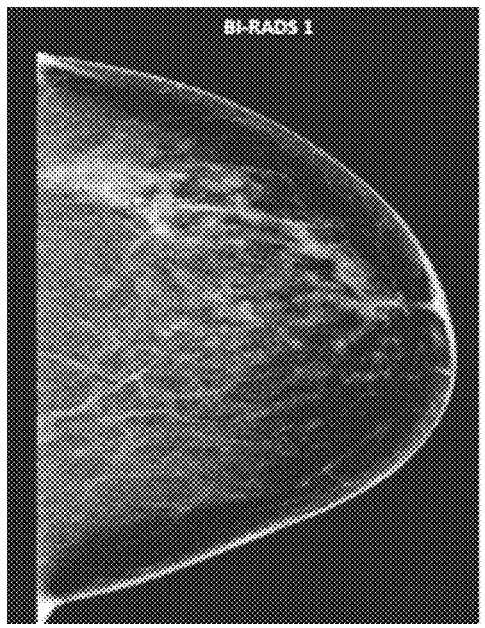
FIG. 4A        FIG. 4B
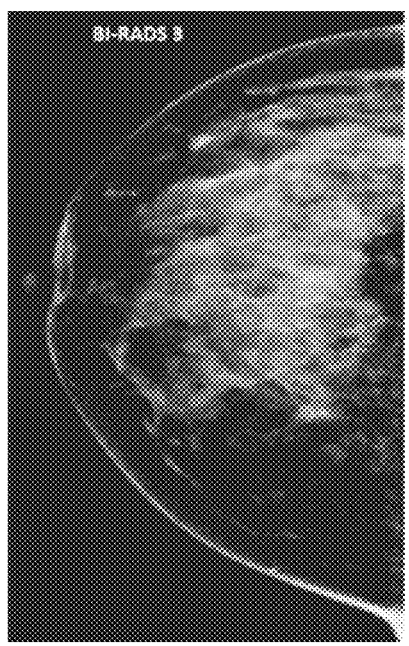
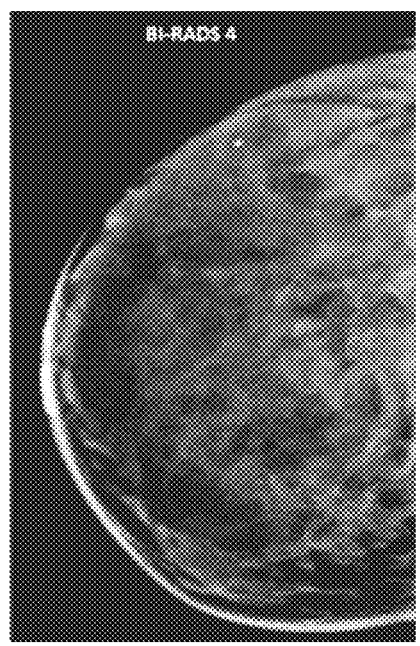
FIG. 4C        FIG. 4D

AUTOMATED FIBRO-GLANDULAR (FG) TISSUE SEGMENTATION IN DIGITAL MAMMOGRAPHY USING FUZZY LOGIC

BACKGROUND OF THE INVENTION

The present invention relates generally to the field of digital mammography, and more particularly to an automated fibro-glandular (FG) tissue segmentation in full digital mammography using a fuzzy logic framework.

Screening mammography is considered to be one of the most reliable and cost-effective methods for the early detection of breast cancer. Breasts are composed of both fatty and fibro-glandular (FG) tissues. Radiologists often look to the FG regions in the breast, to study the patterns and look for abnormalities.

Breast FG density (BD) refers to the prevalence of fibro-glandular tissue in the breast as it appears on a mammogram, and BD estimation is often preceded by FG segmentation. FG tissues may appear in different contrast levels due to many factors, such as projection, mammogram paddle compression force and particular device specifications. At low densities, other anatomic parts, for example, blood vessels and Cooper ligaments strongly resemble the FG tissues in their brightness pattern.

SUMMARY

According to an embodiment of the present invention, a method for segmentation of fibro-glandular (FG) tissue is provided. The method comprises performing, by one or more processors, a training process, the training process comprising: estimating, by one or more processors, a preliminary FG region in a breast domain; extracting, by one or more processors, a set of global features from the breast domain and a set of specific features related to the preliminary FG region and non-FG regions; identifying, by one or more processors, a set of features for breast density discrimination; and configuring, by one or more processors, a fuzzy logic module, wherein the fuzzy logic module is based, in part, on a set of manual settings.

Another embodiment of the present invention provides a computer program product for, based on the method described above.

Another embodiment of the present invention provides a computer system for, based on the method described above.

BRIEF DESCRIPTION OF THE DRAWINGS

FIGS. 4A-D depict four breast density (BD) images, in accordance with an embodiment of the present invention;

DETAILED DESCRIPTION

Embodiments of the present invention provide systems and methods for automated segmentation of the FG tissue in mammography images, by first extracting features from an approximate FG region, then using a fuzzy logic module to compute an adaptive threshold for the segmentation.

Figure 1:
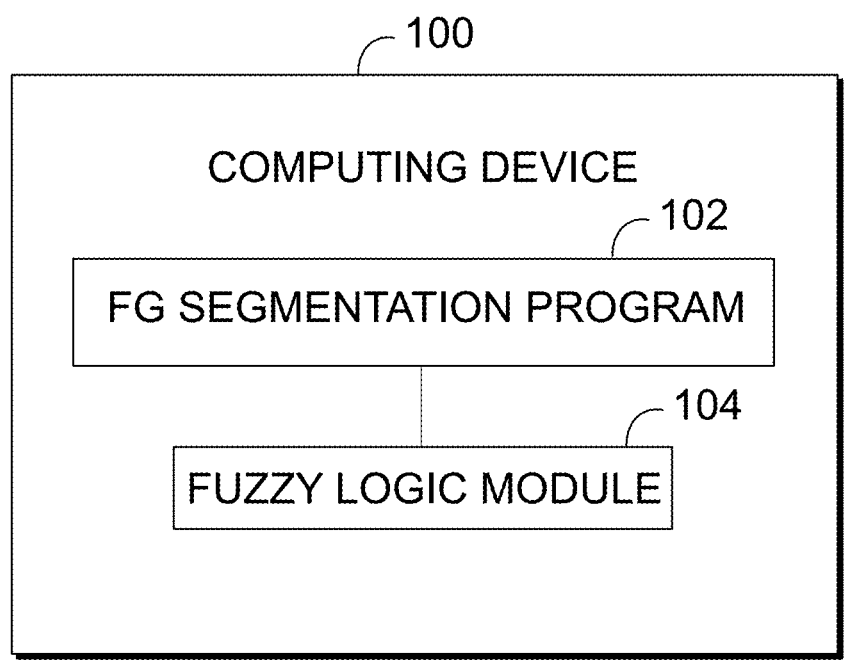
FIG. 1 depicts a block diagram illustrating a computing device, in accordance with an embodiment of the present invention.

The present invention will now be described in detail with reference to the Figures. FIG. 1 depicts a block diagram illustrating a computing device, generally designated 100, in accordance with an embodiment of the present invention. Modifications to computing device 100 may be made by those skilled in the art without departing from the scope of the invention as recited by the claims. In an exemplary embodiment, computing device 100 includes FG segmentation program 102 and fuzzy logic module 104.

In various embodiments of the present invention, computing device 100 can be a laptop computer, a tablet computer, a netbook computer, a personal computer (PC), a desktop computer, a personal digital assistant (PDA), a smart phone, a thin client, a wearable device, or any programmable mobile electronic device capable of executing computer readable program instructions. Computing device 100 may include internal and external hardware components, as depicted and described in further detail with respect to FIG. 7.

FG segmentation program 102 is a software program and can segment an image of a breast using a feature selection method and fuzzy logic module 104. Fuzzy logic module 104 is a software program which provides fuzzy inference of a threshold for image segmentation.

Figure 2A:
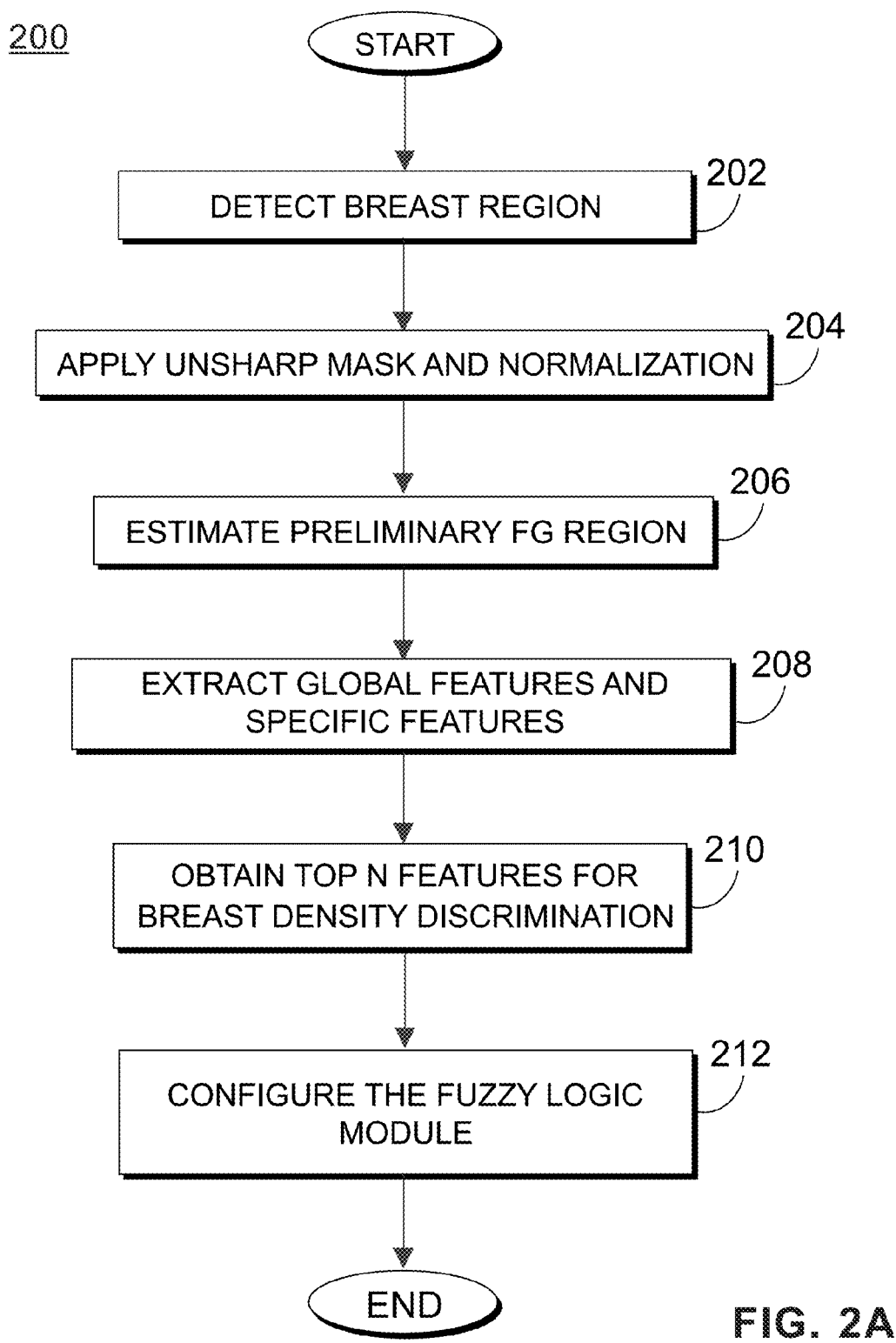
FIG. 2A depicts a flowchart illustrating operational steps for the training process, in accordance with an embodiment of the present invention.

FIG. 2A depicts flowchart 200 illustrating operational steps of FG segmentation program 102 for the training process, in accordance with an embodiment of the present invention.

In step 202, FG segmentation program 102 detects a breast region. In this exemplary embodiment, a set of global features related to the intensity statistics of the breast interior of the image (e.g., a mammography image) are used. For example, the breast outline and pectoral muscle are detected, allowing for the extraction of the relevant breast information from the image.

In step 204, FG segmentation program 102 applies an unsharp mask and performs a normalization. In this exemplary embodiment, an 'unsharp mask filter' is applied to the input image, I, followed by normalization to the range [0,1], in order to extend the discrimination of the FG tissues and sharpen their boundaries, as follows:

$$I_{hpf} = \alpha I - G * I \qquad \text{Equation 1}$$

where $I_{hpf}$ is the relevant breast information replacing the raw gray levels, $\alpha$ is a constant factor, $G$ is a Gaussian, and * denotes standard convolution. However, this process also enhances the non-FG parts, such as blood vessels, mostly visible in fatty breasts, and Cooper ligaments. These false positive regions are factored in at the post-processing stage (i.e., step 234 of FIG. 2B) and will be discussed in further detail later.

In step 206, FG segmentation program 102 estimates a preliminary FG region. In this embodiment, FG segmentation program 102 makes a preliminary estimation of the FG region, based on a preset constant threshold. A threshold, $T \in [0,1]$, on the $I_{hpf}$ image divides the breast interior into two classes (i.e., binarization), where $I_{hpf} > T$ is classified as fibro-glandular (FG) tissue, and the rest is classified as fat. In moderate breast densities (i.e., glandular), the FG tissues are often concentrated in restricted regions, while in more dense breasts, the FG tissue is spread over the breast, is less concentrated, and therefore appears with a lower contrast. By using a constant threshold, moderate breast densities (i.e., BD II & III) can be adequately estimated, however, the constant threshold may over-segment (i.e., false positive) low density breasts and under-segment (i.e., false negative) high density breasts. Thus, while a constant threshold is used at this stage to make a preliminary estimate of the breast density (without having to calculate the actual breast density for each image), an adaptive threshold is set at a later stage (discussed in further detail below) to account for the high and low breast densities. In this exemplary embodiment, the threshold, T, should be in correlation with the breast density.

In step 208, FG segmentation program 102 extracts global features, as well as, specific features. In this exemplary embodiment, FG segmentation program 102 extracts global features from the entire breast domain (i.e., features depend on all of the breast pixels obtained from the image), as well as specific features from the primary FG and fat segments (features depend on only one of the FG and fat segments). The feature set includes the following global features: the first four central moments, intensity range, skew, kurtosis, entropy, breast mean gray level, and area. In this exemplary embodiment, a kernel density estimation is further applied, and the PDF peak levels and localization are extracted, in order to characterize the associated histogram with few descriptors. In order to obtain the region specific features, several geometric properties are used, such as FG area ratio (known as percentage density), as well as Eccentricity, Euler number, Solidity, etc. Another set of features consist of spatial moments, i.e., the position of the FG centroid and fat measured from the nipple (also detected in the process) and the distance between the two. All distances are normalized by the breast inside bounded circle diameter for scale invariance. Having an estimate for FG segmentation, intensity based features can further be derived in the two specific domains of FG and fat, namely, the mean intensities, contrast, difference ratio, and entropy. This feature set provides 38 real value descriptors. The exemplary embodiment can further include clinical features (e.g., age) and machine acquisition measures (e.g., exposure or compression force) for improved performance.

In step 210, FG segmentation program 102 obtains the top n discriminating features in terms of breast density classification. In this embodiment, FG segmentation program 102 uses features selection to obtain the top n number of discriminating features, to be used as the input to fuzzy logic module 104 at a later configuring stage. For example, the top 3 (i.e., n=3) discriminating features may be used.

Figure 3A:
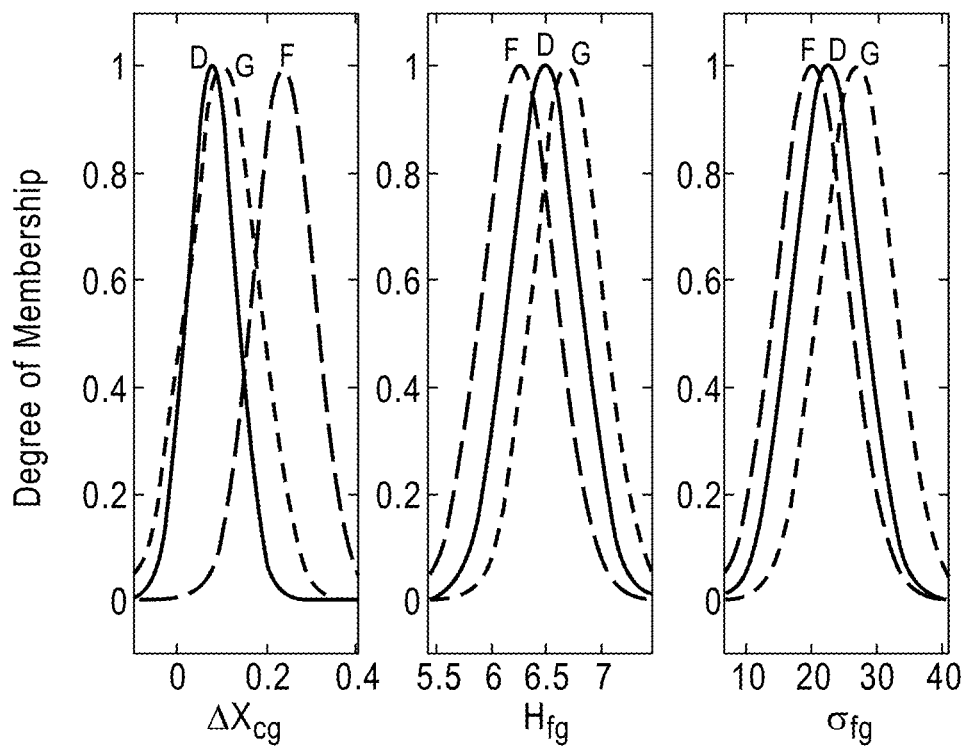
FIG. 3A depicts a graph illustrating the membership functions used with the selected features emerged, in accordance with an embodiment of the present invention.
Figure 3B:
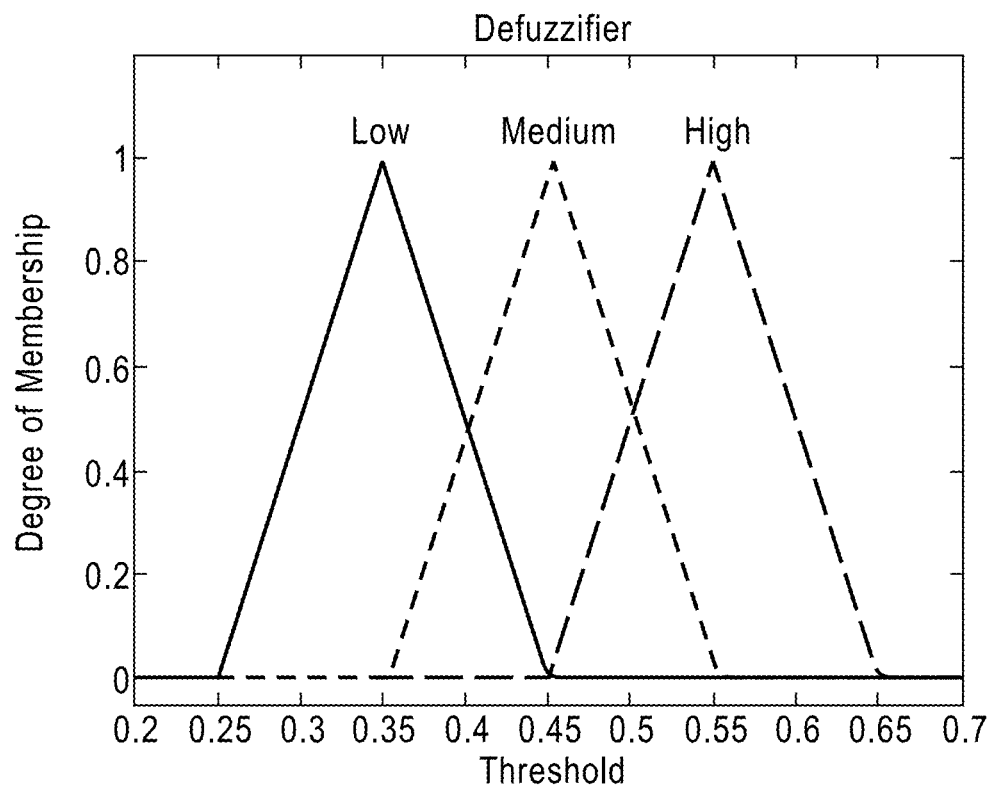
FIG. 3B depicts a graph illustrating a defuzzifier, represented by three functions mapping the fuzzified values from the membership functions to a threshold value, in accordance with an embodiment of the present invention.

In step 212, FG segmentation program 102 configures fuzzy logic module 104. Modern fuzzy logic was developed to model problems in which the rules of inference are formulated in a very general way, making use of diffuse categories. In this embodiment, the input to the fuzzy logic system includes a small subset of features, obtained as the top 3 (i.e., n=3) discriminating features in breast density classification. The process of fuzzy logic involves: membership functions; logical operations; and if-then rules. The membership function of a fuzzy set is a generalization of the indicator function in classical sets representing the degree of membership in a certain class. FIGS. 3A and 3B depict the membership functions used here with the selected features in further detail. The fuzzy logic module 104 outputs a threshold for FG segmentation according to the computed feature vector. This feature vector is first mapped to degree of membership by the fuzzifier (i.e., FIG. 3A). The fuzzy membership vector is then inserted into the defuzzifier function (FIG. 3B) to yield the desired segmentation threshold.

In this exemplary embodiment, a filter map of the image is first obtained using the unsharp mask in order to emphasize high frequencies in the image. A pre-configured fuzzy logic scheme is then used, based on the chosen most informative features, to estimate the breast density and the resulting threshold. The configuration stage is a well-known procedure in FL approach, consisting of the generation of fuzzy rules by a trained personnel. While this process is still manual, it is significantly less time consuming than annotation of hundreds of images and can further be conducted by inexpert personnel.

Figure 2B:
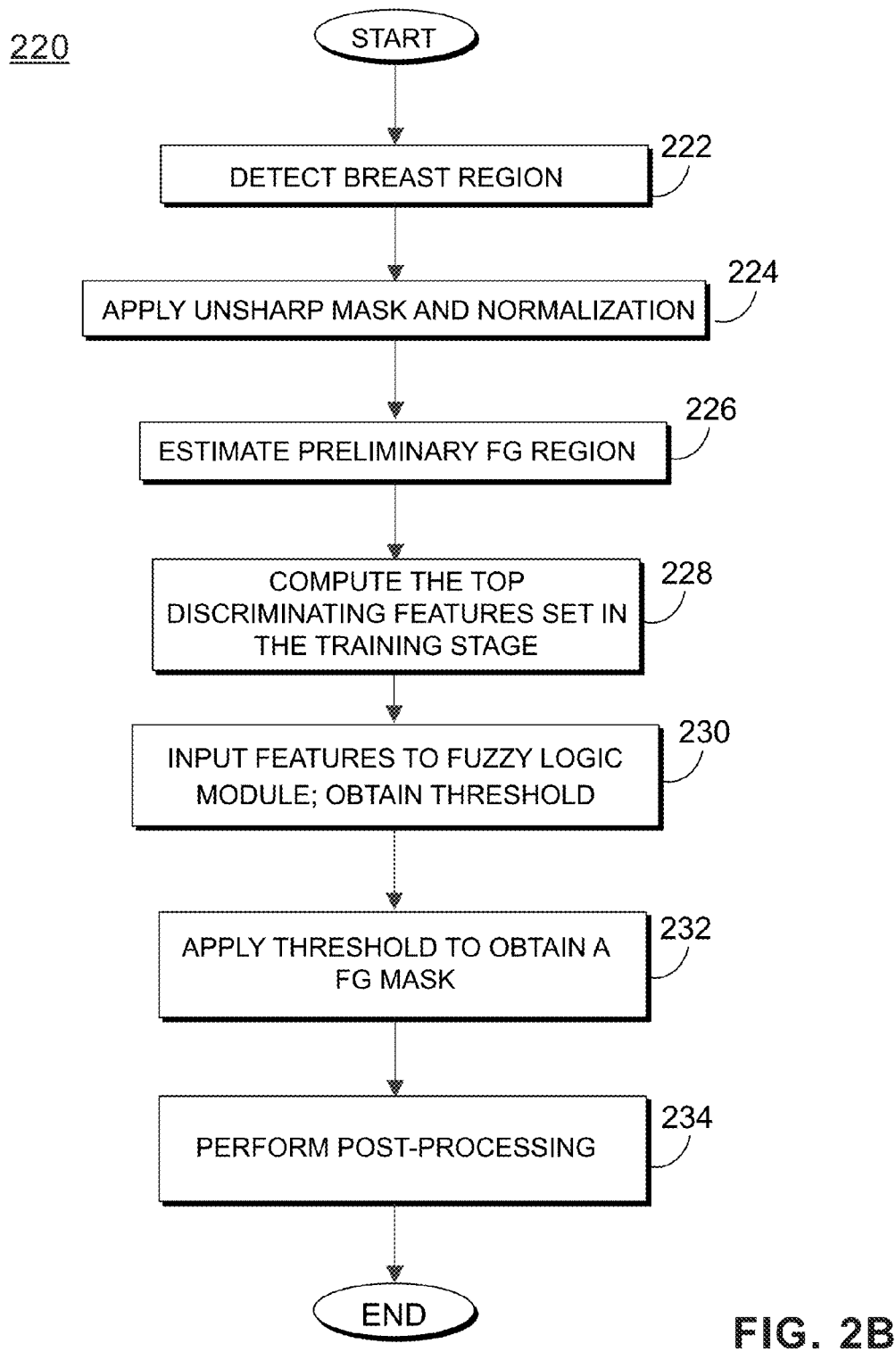
FIG. 2B depicts a flowchart illustrating operational steps for the testing process, in accordance with an embodiment of the present invention.

FIG. 2B depicts a flowchart 220 illustrating operational steps for the testing process (i.e., processing input in production), in accordance with an embodiment of the present invention.

In step 222, FG segmentation program 102 detects a breast region. In this exemplary embodiment, a set of global features related to the intensity statistics of the breast interior of the image (e.g., a mammography image) are used. For example, the breast outline and pectoral muscle are detected, allowing for the extraction of the relevant breast information from the image.

In step 224, FG segmentation program 102 applies an unsharp mask and performs a normalization. In this exemplary embodiment, an 'unsharp mask filter' is applied to the input image, I, followed by normalization to the range [0,1], in order to extend the discrimination of the FG tissues and sharpen their boundaries, as was applied in step 204 of FIG. 2A, above. However, this process also enhances the non-FG parts, such as blood vessels, mostly visible in fatty breasts, and Cooper ligaments. These false positive regions are factored in at the post-processing stage (i.e., step 234) and will be discussed in further detail later.

In step 226 FG segmentation program 102 estimates a preliminary FG region. In this embodiment, FG segmentation program 102 makes a preliminary estimation of the FG region, based on a preset constant threshold, following the same process as described above with respect to step 206 of FIG. 2A.

In step 228, FG segmentation program 102 computes the top discriminating features set in the training stage. In this embodiment, in order to determine the top discriminating features, a Random-Forest classifier is used on a training set, which is divided into three density categories: Fatty-F (BD-I); Glandular-G (BD-II & BD-III); and Dense-D (BD-IV). Only the top discriminating features found in the training process (i.e., FIG. 2A) are computed and used at the test stage.

In step 230, FG segmentation program 102 inputs features into fuzzy logic module 104 and obtains a threshold. In this exemplary embodiment, FG segmentation program 102 inputs the identified top discriminating features into the configured fuzzy logic module 104 and obtains a threshold for segmentation.

In step 232, FG segmentation program 102 applies the threshold to obtain an FG mask. In this exemplary embodiment, FG segmentation program 102 then imposes a threshold on a filtered version of the image. In this exemplary embodiment, the threshold is applied on the filtered image to yield a mask, then goes through further post-processing steps.

In step 234, FG segmentation program 102 performs post processing, in order to reduce miss-classified regions. One aspect of post-processing deals with non-FG parts which may have been misclassified during the FG segmentation after applying the adaptive threshold (i.e., step 232). In order to account for these false positives, their geometrical characteristics are exploited as an elongated structure. In this exemplary embodiment, FG segmentation program 102 applies a connected-components on the derived FG mask and removes the parts having a distance transform of less than a certain threshold. This process is aimed to reject elongated structures from the FG mask, such as blood vessels and Cooper ligaments, which exhibit similar gray levels to FG tissues in the image. The post-processing operations are ended by morphological hole-filling, in order to provide the desirable simply-connected regions.

Accordingly, by performing the operational steps of FIGS. 2A and 2B, an efficient and automated method for FG tissue segmentation in digital mammography is achieved, by extracting features from a primary stage of an approximately correct segmentation, allowing for fuzzy identification of the breast density used to compute an adaptive threshold for segmentation.

FIG. 3A depicts a graph illustrating the membership functions used with the selected features emerged, in accordance with an embodiment of the present invention.

As depicted in FIG. 3A the membership functions used herein with the selected features emerged as: $\Delta X_{cg}$ (FG-fat centroid distance); $H_{FG}$ (FG entropy), and $\sigma_{FG}$ (FG intensity standard deviation). This feature ranking shows that the FG-fat centroid distance can be associated with the method or data bias in the constant threshold segmentation. In this exemplary embodiment, the following rules are set according to the observed membership functions: (i) If $\Delta X_{cg}$ is F and $H_{fg}$ is F then T is high; (ii) If $\Delta X_{cg}$ is G and $H_{fg}$ is G and $\sigma_{FG}$ is G, then T is medium; and (iii) If $\Delta X_{cg}$ is D and $H_{fg}$ is D then T is low.

FIG. 3B depicts a graph illustrating a defuzzifier, represented by three triangular functions mapping the fuzzified values from the membership functions to a threshold value, in accordance with an embodiment of the present invention.

In this exemplary embodiment, given a test image, the selected features are computed and set as input to the fuzzy logic module 104, which yields a threshold according to degree of memberships to different BD categories, fatty (F), glandular (G), or dense (D). As depicted in FIG. 3B, there are three threshold levels (i.e., low, medium, and high), which are associated with high BD, medium BD, and low BD, respectively.

FIGS. 4A-D depict the relationship between contrast and breast density (BD), as described above. FIGS. 4A-D each depict a different breast density image (from breast-imaging reporting and data systems or BI-RADS), showing the low contrast appearance of FG tissues in BI-RADS 4 (high breast densities), while non-FG tissues, such as veins and Cooper ligaments, tend to be more eminent in low breast densities (i.e., BI-RADS 1). To account for these differences in densities, the present invention makes use of an adaptive threshold, as described above.

Figure 5C:
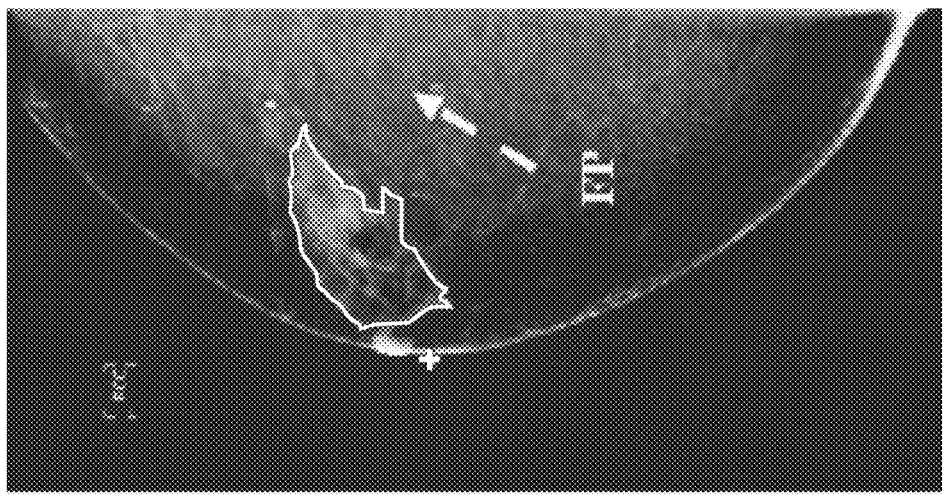
FIGS. 5A-F depict images illustrating the impact of the adaptive threshold, in accordance with an embodiment of the present invention.
Figure 5B:
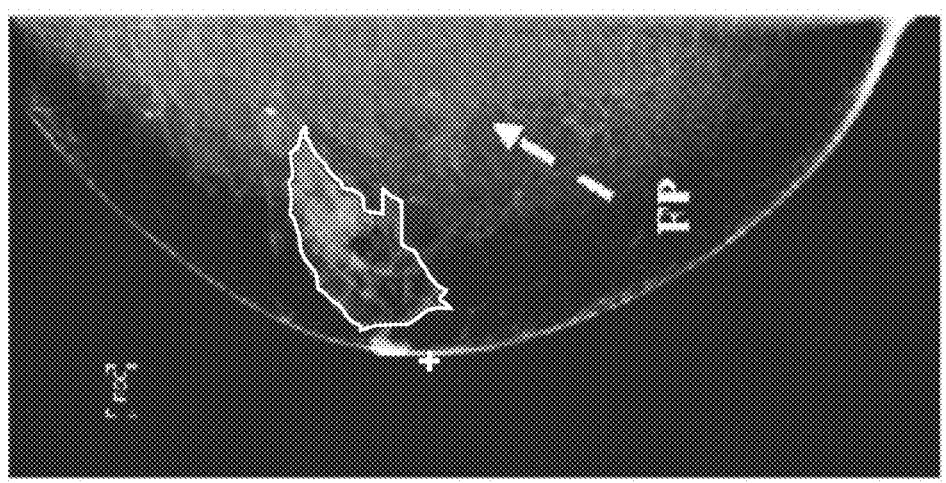
Figure 5A:
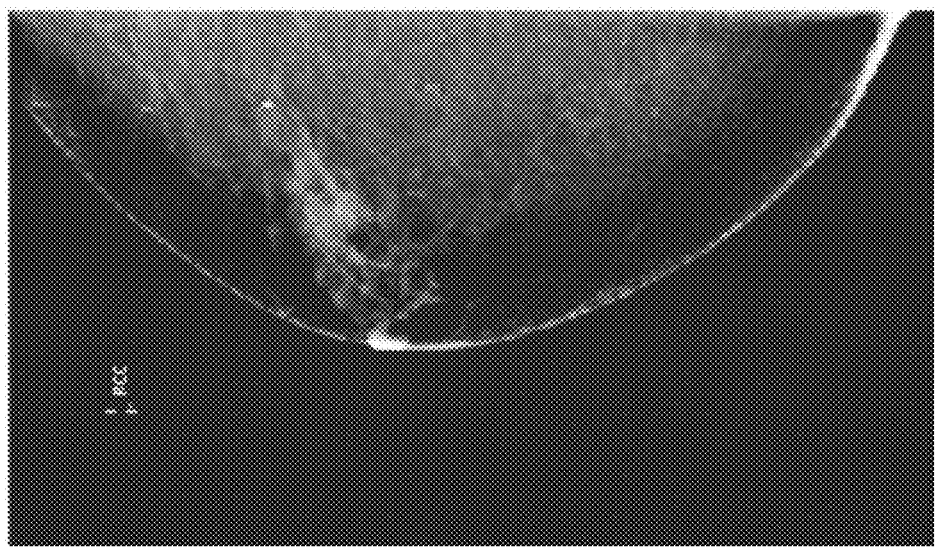
Figure 5F:
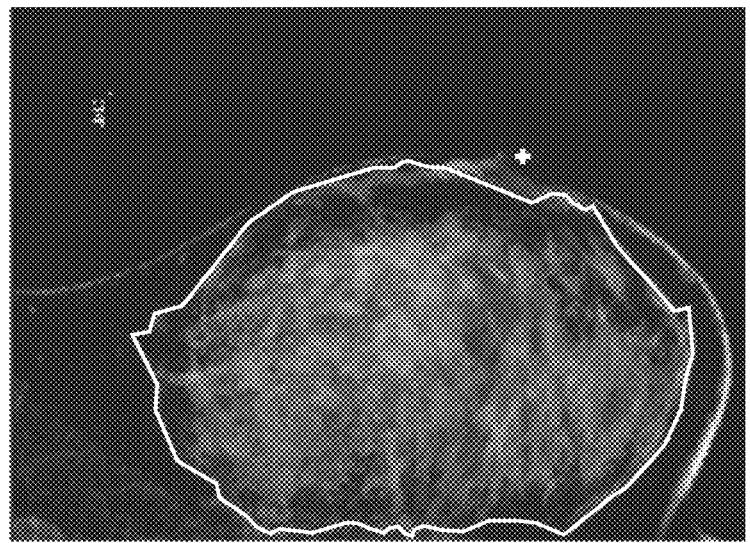
Figure 5E:
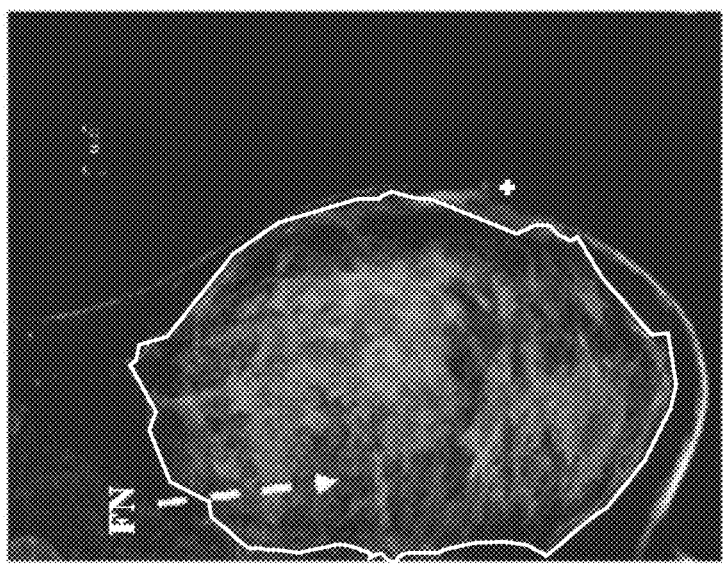
Figure 5D:
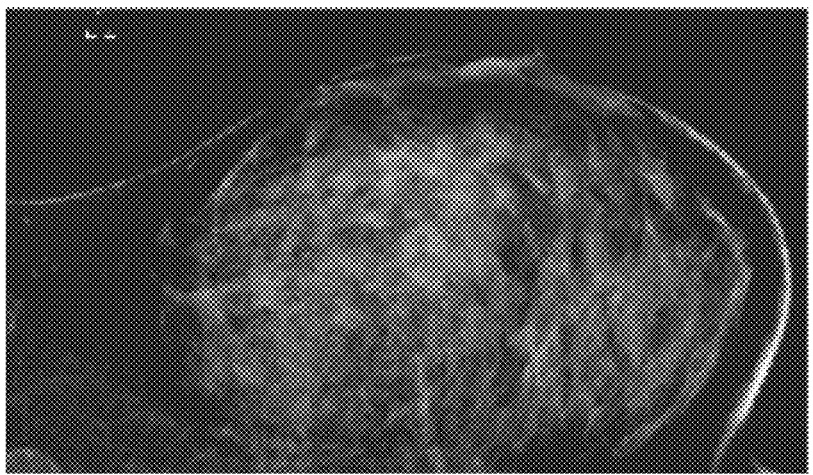

FIGS. 5A-C depict images illustrating the impact of the adaptive threshold, in accordance with an embodiment of the present invention. FIGS. 5A-C depict image samples for a fatty breast, while FIGS. 5D-F depict image samples for a dense breast.

Often, the percentage density (the size of FG mask with respect to the breast) is directly used to classify a given mammogram to a certain density category. However, a simple ratio of the tissue mask could not be significantly informative to correctly classify the breast, due to the fact that texture properties play an important role. Therefore, all of the extracted features, as described above, are included in the classification method, chosen as Random-forest, with internal feature selection scheme. The resulting breast density classification accuracies are described in Table 1 with comparison to the constant threshold alternative where the suggested Fuzzy logic module is not considered. In obtaining the accuracies in Table 1, a large database of digital mammograms was used, containing 1243 images, 688 CC, and 555 MLO views from 589 women. The data distribution among the classes was 21% BD-I, 44% BD-II, 28% BD-III, and 7% BD-IV. The measures in Table 1 are based on k=5 fold cross-validation. The results indicate that on average, the accuracy is improved by the proposed methods from 67.4% to 75%. The improvement is mostly obtained in low densities where prevention of false-positive detection of FG tissues avoids these samples to be classified with higher breast densities. For BD categories III and IV the performance is comparable. The Low and High columns describe the accuracies for binary classification case.

TABLE 1

| Threshold | B-I | B-II | B-III | B-IV | Total | Low | High |
| --- | --- | --- | --- | --- | --- | --- | --- |
| Constant | 69.4% | 72.1% | 66.8% | 40.0% | 67.4% | 86.7% | 73.3% |
| Adaptive | 81.1% | 83.3% | 65.9% | 41.7% | 75.0% | 90.0% | 72.0% |

Figure 6:
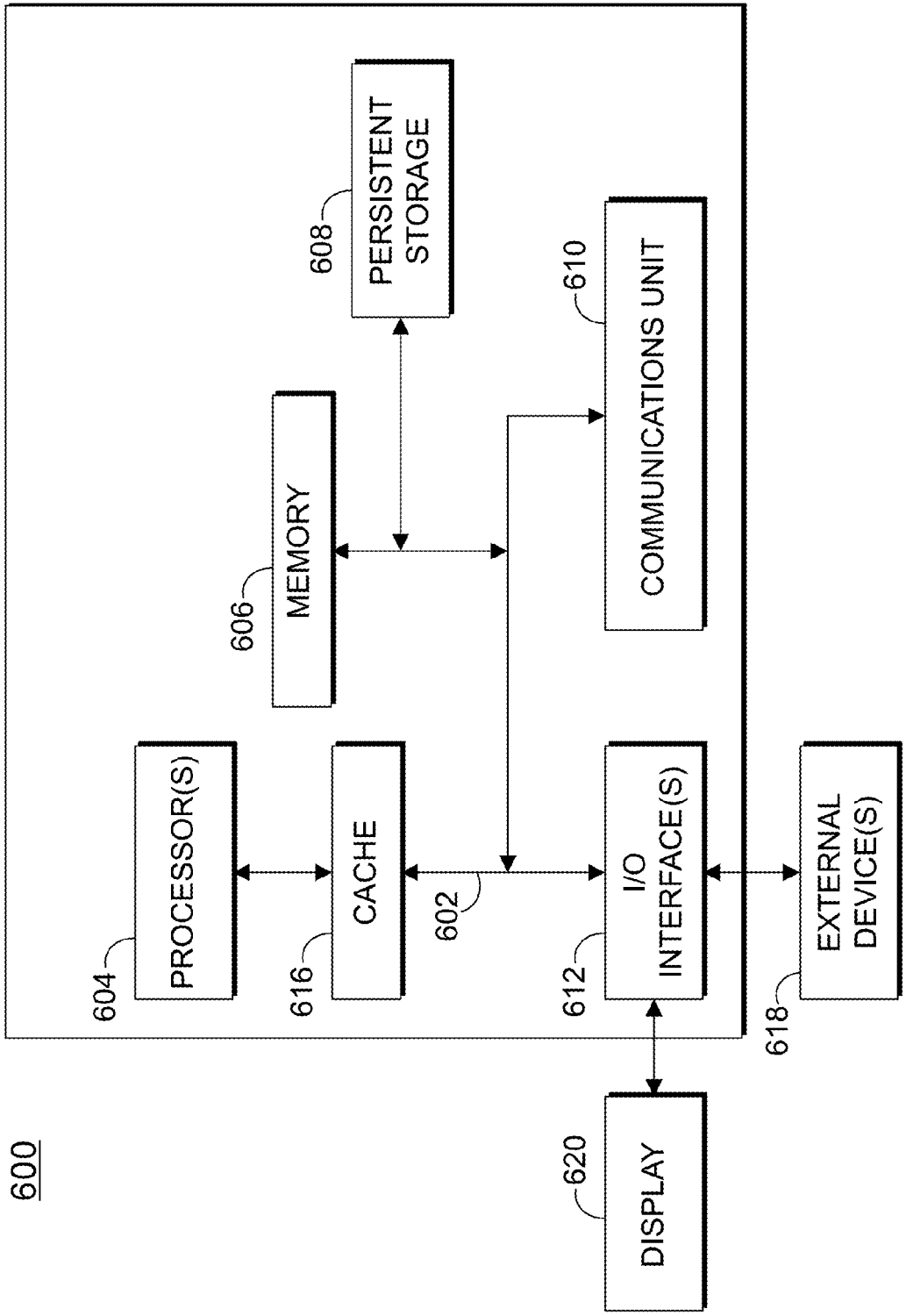
FIG. 6 depicts a block diagram of components of a computing device, in accordance with an illustrative embodiment of the present invention.

FIG. 6 is a block diagram of internal and external components of a computing device, generally designated 600, which is representative of the computing device of FIG. 1, in accordance with an embodiment of the present invention. It should be appreciated that FIG. 6 provides only an illustration of one implementation and does not imply any limitations with regard to the environments in which different embodiments may be implemented. Many modifications to the depicted environment may be made.

Computing device 600 includes communications fabric 608, which provides communications between computer processor(s) 602, memory 604, cache 606, persistent storage 610, communications unit 614, and input/output (I/O) interface(s) 612. Communications fabric 608 can be implemented with any architecture designed for passing data and/or control information between processors (such as microprocessors, communications and network processors, etc.), system memory, peripheral devices, and any other hardware components within a system. For example, communications fabric 608 can be implemented with one or more buses.

Memory 604 and persistent storage 610 are computer-readable storage media. In this embodiment, memory 604 includes random access memory (RAM). In general, memory 604 can include any suitable volatile or non-volatile computer readable storage media. Cache 606 is a fast memory that enhances the performance of processors 602 by holding recently accessed data, and data near recently accessed data, from memory 604.

Program instructions and data used to practice embodiments of the present invention may be stored in persistent storage 610 and in memory 604 for execution by one or more of the respective processors 602 via cache 606. In an embodiment, persistent storage 610 includes a magnetic hard disk drive. Alternatively, or in addition to a magnetic hard disk drive, persistent storage 610 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 610 may also be removable. For example, a removable hard drive may be used for persistent storage 610. Other examples include optical and magnetic disks, thumb drives, and smart cards that are inserted into a drive for transfer onto another computer readable storage medium that is also part of persistent storage 610.

Communications unit 614, in these examples, provides for communications with other data processing systems or devices, including resources of a network. In these examples, communications unit 614 includes one or more network interface cards. Communications unit 614 may provide communications through the use of either or both physical and wireless communications links. Program instructions and data used to practice embodiments of the present invention may be downloaded to persistent storage 610 through communications unit 614.

I/O interface(s) 612 allows for input and output of data with other devices that may be connected to computing device 600. For example, I/O interface 612 may provide a connection to external devices 616 such as a keyboard, keypad, a touch screen, and/or some other suitable input device. External devices 616 can also include portable computer-readable storage media such as, for example, thumb drives, portable optical or magnetic disks, and memory cards. Software and data used to practice embodiments of the present invention (e.g., software and data) can be stored on such portable computer-readable storage media and can be loaded onto persistent storage 610 via I/O interface(s) 612. I/O interface(s) 612 also connect to a display 618.

Display 618 provides a mechanism to display data to a user and may be, for example, a computer monitor, or a television screen.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for segmentation of fibro-glandular (FG) tissue, the method comprising:
    performing, by one or more processors, a training process, the training process comprising:
        estimating, by one or more processors, a preliminary FG region in a breast domain;
        extracting, by one or more processors, a set of global features from the breast domain and a set of specific features related to the preliminary FG region and non-FG regions;
        identifying, by one or more processors, a set of features for breast density discrimination;
        configuring, by one or more processors, a fuzzy logic module, wherein the fuzzy logic module is based, in part, on a set of manual settings;
        computing, by one or more processors, the identified set of features for breast density discrimination, set in the training process;
        inputting, by one or more processors, the computed set of features for breast density discrimination into the configured fuzzy logic module, to obtain a threshold;
        applying, by one or more processors, the obtained threshold to derive an FG mask, and
        performing, by one or more processors, post-processing on the derived FG mask.

2. The method of claim 1, wherein estimating a preliminary FG region in a breast domain is based on a predefined constant threshold, and wherein the obtained threshold is based on an adaptive threshold, which accounts for differences in breast densities.

3. The method of claim 1, wherein performing post-processing on the derived FG mask comprises:
    extracting, by one or more computer processors, a connected component of the derived FG mask of a breast image; and
    removing, by one or more computer processors, a connected component having a maximum distance transform value of less than a predetermined threshold.

4. The method of claim 1, wherein identifying a set of features for breast density discrimination comprises:
    using, by one or more processors, a feature selection to obtain a number of discriminating features, wherein the obtained number of discriminating features are used as input to the fuzzy logic module, and wherein the feature selection comprises a Random-Forest classifier.

5. The method of claim 1, wherein the set of global features comprises one of the following features: first four central moments, intensity range, skew, kurtosis, entropy, breast mean gray level, and area.

6. The method of claim 1, wherein the set of specific features comprise one of the following features: geometric properties and spatial moments.

7. A computer program product for segmentation of fibro-glandular (FG) tissue, the computer program product comprising:
    a computer readable storage medium and program instructions stored on the computer readable storage medium, the program instructions comprising:
    program instructions to perform a training process, the training process comprising:
    program instructions to estimate a preliminary FG region in a breast domain;
    program instructions to extract a set of global features from the breast domain and a set of specific features related to the preliminary FG region and non-FG regions;
    program instructions to identify a set of features for breast density discrimination;
    program instructions to configure a fuzzy logic module, wherein the fuzzy logic module is based, in part, on a set of manual settings;
    program instructions to compute the identified set of features for breast density discrimination set in the training process;
    program instructions to input the computed set of features for breast density discrimination into the configured fuzzy logic module, to obtain a threshold;

program instructions to apply the obtained threshold to derive an FG mask; and program instructions to perform post-processing on the derived FG mask.

8. The computer program product of claim 7, wherein the program instructions to estimate a preliminary FG region in a breast domain is based on a predefined constant threshold, and wherein the obtained threshold is based on an adaptive threshold, which accounts for differences in breast densities.

9. The computer program product of claim 7, wherein the program instructions to perform post-processing on the derived FG mask comprise:

program instructions to extract a connected component of the derived FG mask of a breast image; and program instructions to remove a connected component having a maximum distance transform value of less than a predetermined threshold.

10. The computer program product of claim 7, wherein the program instructions to identify a set of features for breast density discrimination comprise:

program instructions to use a feature selection to obtain a number of discriminating features, wherein the obtained number of discriminating features are used as input to the fuzzy logic module, and wherein the feature selection comprises a Random-Forest classifier.

11. The computer program product of claim 7, wherein the set of global features comprises one of the following features: first four central moments, intensity range, skew, kurtosis, entropy, breast mean gray level, and area.

12. The computer program product of claim 7, wherein the set of specific features comprise one of the following features: geometric properties and spatial moments.

13. A computer system for segmentation of fibro-glandular (FG) tissue, the computer system comprising:

one or more computer processors;

one or more computer readable storage media; and program instructions stored on the one or more computer readable storage media for execution by at least one of the one or more processors, the program instructions comprising:

program instructions to perform a training process, the training process comprising:

program instructions to estimate a preliminary FG region in a breast domain;

program instructions to extract a set of global features from the breast domain and a set of specific features related to the preliminary FG region and non-FG regions;

program instructions to identify a set of features for breast density discrimination;

program instructions to configure a fuzzy logic module, wherein the fuzzy logic module is based, in part, on a set of manual settings;

program instructions to compute the identified set of features for breast density discrimination, set in the training process;

program instructions to input the computed set of features for breast density discrimination into the configured fuzzy logic module, to obtain a threshold;

program instructions to apply the obtained threshold to derive an FG mask; and program instructions to perform post-processing on the derived FG mask.

14. The computer system of claim 13, wherein the program instructions to estimate a preliminary FG region in a breast domain is based on a predefined constant threshold, and wherein the obtained threshold is based on an adaptive threshold, which accounts for differences in breast densities.

15. The computer system of claim 13, wherein the program instructions to perform post-processing on the derived FG mask comprise:

program instructions to extract a connected component of the derived FG mask of a breast image; and program instructions to remove a connected component having a maximum distance transform value of less than a predetermined threshold.

16. The computer system of claim 13, wherein the program instructions to identify a set of features for breast density discrimination comprise:

program instructions to use a feature selection to obtain a number of discriminating features, wherein the obtained number of discriminating features are used as input to the fuzzy logic module, and wherein the feature selection comprises a Random-Forest classifier.

17. The computer system of claim 13, wherein the set of global features comprises one of the following features: first four central moments, intensity range, skew, kurtosis, entropy, breast mean gray level, and area.

* * * * *